United States Patent
Weinberg et al.

(10) Patent No.: US 10,582,964 B2
(45) Date of Patent: Mar. 10, 2020

(54) METHOD AND SYSTEM FOR CONTROLLING AN OUTPUT OF A RADIO-FREQUENCY MEDICAL GENERATOR HAVING AN IMPEDANCE BASED CONTROL ALGORITHM

(71) Applicant: COVIDIEN AG, Neuhausen am Rheinfall (CH)

(72) Inventors: Craig Weinberg, Denver, CO (US); Kari Leidich, Golden, CO (US)

(73) Assignee: Covidien LP, Mansfield, MA (US)

( * ) Notice: Subject to any disclaimer, the term of this patent is extended or adjusted under 35 U.S.C. 154(b) by 369 days.

(21) Appl. No.: 15/586,871

(22) Filed: May 4, 2017

(65) Prior Publication Data
US 2017/0231685 A1 Aug. 17, 2017

Related U.S. Application Data

(63) Continuation of application No. 14/192,112, filed on Feb. 27, 2014, now Pat. No. 9,642,665, which is a
(Continued)

(51) Int. Cl.
*A61B 18/12* (2006.01)
*A61B 18/00* (2006.01)

(52) U.S. Cl.
CPC .......... *A61B 18/1233* (2013.01); *A61B 18/00* (2013.01); *A61B 18/1206* (2013.01);
(Continued)

(58) Field of Classification Search
CPC . A61B 18/00; A61B 18/1206; A61B 18/1233; A61B 2018/00648;
(Continued)

(56) References Cited

U.S. PATENT DOCUMENTS

| 1,787,709 A | 1/1931 | Wappler |
| 1,813,902 A | 7/1931 | Bovie |

(Continued)

FOREIGN PATENT DOCUMENTS

| DE | 179607 C | 3/1905 |
| DE | 390937 C | 3/1924 |

(Continued)

OTHER PUBLICATIONS

International Search Report EP08012503 dated Sep. 19, 2008.
(Continued)

*Primary Examiner* — Michael F Peffley

(57) ABSTRACT

A system for performing an electrosurgical procedure at a surgical site is disclosed. The system includes a sensor configured to continually sense an electrical and/or a physical property of tissue at a surgical site and to generate a sensor signal as a function thereof. The system also includes a control module configured to process the sensor signal using a processor, an algorithm, and a map having one or more predetermined values. The control module is further configured to compare the sensor signal to a predetermined level to determine reliability of the sensor signal and to signal an electrosurgical generator in response to a reliable sensor signal such that the electrosurgical generator enters energy control mode, wherein the electrosurgical generator matches an output of the control signal with a predetermined value from the map.

14 Claims, 7 Drawing Sheets

Related U.S. Application Data continuation of application No. 11/657,173, filed on Jan. 24, 2007, now Pat. No. 8,663,214.

(60) Provisional application No. 60/761,498, filed on Jan. 24, 2006.

(52) U.S. Cl.
CPC .............. *A61B 2018/00648* (2013.01); *A61B 2018/00702* (2013.01); *A61B 2018/00726* (2013.01); *A61B 2018/00767* (2013.01); *A61B 2018/00791* (2013.01); *A61B 2018/00827* (2013.01); *A61B 2018/00875* (2013.01); *A61B 2018/00892* (2013.01)

(58) Field of Classification Search
CPC .......................... A61B 2018/00702; A61B 2018/00726; A61B 2018/00767; A61B 2018/00791; A61B 2018/00827; A61B 2018/00875; A61B 2018/00892
See application file for complete search history.

(56) References Cited

U.S. PATENT DOCUMENTS

| | | |
|---|---|---|
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko et al. |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gonser |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,496 A | 12/1985 | Hamden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |

(56) References Cited

U.S. PATENT DOCUMENTS

| | | |
|---|---|---|
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,767,999 A | 8/1988 | VerPlanck |
| 4,768,969 A | 9/1988 | Bauer et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Kllcek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,463 A | 8/1995 | Stern et al. |
| 5,445,635 A | 8/1995 | Denen et al. |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |

(56) References Cited

U.S. PATENT DOCUMENTS

| | | |
|---|---|---|
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,788,688 A | 8/1998 | Bauer et al. |
| 5,792,138 A | 8/1998 | Shipp |
| 5,797,902 A | 8/1998 | Netherly |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,836 A | 8/1999 | Hatta et al. |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,959,253 A | 9/1999 | Shinchi |
| 5,961,344 A | 10/1999 | Rosales et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 6,007,532 A | 12/1999 | Netherly |
| 6,010,499 A | 1/2000 | Cobb |
| 6,013,074 A | 1/2000 | Taylor |
| 6,014,581 A | 1/2000 | Whayne et al. |
| 6,017,338 A | 1/2000 | Brucker et al. |
| 6,022,346 A | 2/2000 | Panescu et al. |
| 6,022,347 A | 2/2000 | Lindenmeier et al. |
| 6,033,399 A | 3/2000 | Gines |
| 6,039,731 A | 3/2000 | Taylor et al. |
| 6,039,732 A | 3/2000 | Ichikawa et al. |
| 6,041,260 A | 3/2000 | Stern et al. |
| 6,044,283 A | 3/2000 | Fein et al. |
| 6,053,910 A | 4/2000 | Fleenor |
| 6,053,912 A | 4/2000 | Panescu et al. |
| 6,055,458 A | 4/2000 | Cochran et al. |
| 6,056,745 A | 5/2000 | Panescu et al. |
| 6,056,746 A | 5/2000 | Goble et al. |
| 6,059,781 A | 5/2000 | Yamanashi et al. |
| 6,063,075 A | 5/2000 | Mihori |
| 6,063,078 A | 5/2000 | Wittkampf |
| 6,066,137 A | 5/2000 | Greep |
| 6,068,627 A | 5/2000 | Orszulak et al. |
| 6,074,089 A | 6/2000 | Hollander et al. |
| 6,074,386 A | 6/2000 | Goble et al. |
| 6,074,388 A | 6/2000 | Tockweiler et al. |
| 6,080,149 A | 6/2000 | Huang et al. |
| 6,088,614 A | 7/2000 | Swanson |
| 6,093,186 A | 7/2000 | Goble |
| 6,102,497 A | 8/2000 | Ehr et al. |
| 6,102,907 A | 8/2000 | Smethers et al. |
| 6,113,591 A | 9/2000 | Whayne et al. |
| 6,113,592 A | 9/2000 | Taylor |
| 6,113,593 A | 9/2000 | Tu et al. |
| 6,113,596 A | 9/2000 | Hooven et al. |
| 6,123,701 A | 9/2000 | Nezhat |
| 6,123,702 A | 9/2000 | Swanson et al. |
| 6,132,429 A | 10/2000 | Baker |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,171,304 B1 | 1/2001 | Netherly et al. |
| 6,183,468 B1 | 2/2001 | Swanson et al. |

(56) References Cited

U.S. PATENT DOCUMENTS

| | | |
|---|---|---|
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek et al. |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman et al. |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu et al. |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards et al. |
| 6,275,786 B1 | 8/2001 | Daners |
| 6,293,941 B1 | 9/2001 | Strul et al. |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards et al. |
| 6,364,877 B1 | 4/2002 | Goble et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 * | 6/2002 | Buysse .............. A61B 18/1445 606/34 |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock et al. |
| 6,458,122 B1 | 10/2002 | Pozzato |
| 6,464,689 B1 | 10/2002 | Qin et al. |
| 6,464,696 B1 | 10/2002 | Oyama et al. |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul et al. |
| 6,511,476 B2 | 1/2003 | Hareyama |
| 6,511,478 B1 | 1/2003 | Burnside et al. |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 * | 4/2003 | Goldin .............. A61B 18/12 600/374 |
| 6,546,370 B2 | 4/2003 | Heo |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton et al. |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai et al. |
| 6,626,901 B1 | 9/2003 | Treat et al. |
| 6,629,973 B1 | 10/2003 | Wårdell et al. |
| 6,632,193 B1 | 10/2003 | Davison et al. |
| 6,635,056 B2 | 10/2003 | Kadhiresan et al. |
| 6,635,057 B2 | 10/2003 | Harano et al. |
| 6,645,198 B1 | 11/2003 | Bommannan et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,514 B2 | 11/2003 | Ellman et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim et al. |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman et al. |
| 6,730,078 B2 | 5/2004 | Simpson et al. |
| 6,730,079 B2 | 5/2004 | Lovewell |
| 6,730,080 B2 | 5/2004 | Harano et al. |
| 6,733,495 B1 | 5/2004 | Bek et al. |
| 6,733,498 B2 | 5/2004 | Paton et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,790,206 B2 | 9/2004 | Panescu |

(56) References Cited

U.S. PATENT DOCUMENTS

| | | |
|---|---|---|
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano et al. |
| 6,860,881 B2 | 3/2005 | Sturm et al. |
| 6,864,686 B2 | 3/2005 | Novak et al. |
| 6,875,210 B2 | 4/2005 | Refior et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,958,064 B2 | 10/2005 | Rioux et al. |
| 6,962,587 B2 | 11/2005 | Johnson et al. |
| 6,966,907 B2 | 11/2005 | Goble |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 8,663,214 B2 | 3/2014 | Weinberg et al. |
| 9,642,665 B2 | 5/2017 | Weinberg et al. |
| 2001/0014804 A1 | 8/2001 | Goble et al. |
| 2001/0029315 A1 | 10/2001 | Sakurai et al. |
| 2001/0031962 A1 | 10/2001 | Eggleston |
| 2002/0035363 A1 | 3/2002 | Edwards et al. |
| 2002/0035364 A1 | 3/2002 | Schoenman et al. |
| 2002/0052599 A1 | 5/2002 | Goble |
| 2002/0068932 A1 | 6/2002 | Edwards et al. |
| 2002/0107517 A1 | 8/2002 | Witt et al. |
| 2002/0111624 A1 | 8/2002 | Witt et al. |
| 2002/0151889 A1 | 10/2002 | Swanson et al. |
| 2002/0193787 A1 | 12/2002 | Qin et al. |
| 2003/0004510 A1 | 1/2003 | Wham et al. |
| 2003/0060818 A1 | 3/2003 | Kannenberg et al. |
| 2003/0078572 A1 | 4/2003 | Pearson et al. |
| 2003/0139741 A1 | 7/2003 | Goble et al. |
| 2003/0153908 A1 | 8/2003 | Goble et al. |
| 2003/0163123 A1 | 8/2003 | Goble et al. |
| 2003/0163124 A1 | 8/2003 | Goble |
| 2003/0171745 A1 | 9/2003 | Francischelli et al. |
| 2003/0181898 A1 | 9/2003 | Bowers |

(56) References Cited

U.S. PATENT DOCUMENTS

| | | |
|---|---|---|
| 2003/0199863 A1 | 10/2003 | Swanson et al. |
| 2003/0225401 A1 | 12/2003 | Eggers et al. |
| 2004/0002745 A1 | 1/2004 | Fleming et al. |
| 2004/0015159 A1 | 1/2004 | Slater et al. |
| 2004/0015163 A1 | 1/2004 | Buysse et al. |
| 2004/0015216 A1 | 1/2004 | DeSisto |
| 2004/0019347 A1 | 1/2004 | Sakurai et al. |
| 2004/0024395 A1 | 2/2004 | Ellman et al. |
| 2004/0030328 A1 | 2/2004 | Eggers et al. |
| 2004/0030330 A1 | 2/2004 | Brassell et al. |
| 2004/0044339 A1 | 3/2004 | Beller et al. |
| 2004/0049179 A1 | 3/2004 | Francischelli et al. |
| 2004/0054365 A1 | 3/2004 | Goble |
| 2004/0059323 A1 | 3/2004 | Sturm et al. |
| 2004/0068304 A1 | 4/2004 | Paton et al. |
| 2004/0082946 A1 | 4/2004 | Malis et al. |
| 2004/0095100 A1 | 5/2004 | Thompson |
| 2004/0097912 A1 | 5/2004 | Gonnering |
| 2004/0097914 A1 | 5/2004 | Pantera et al. |
| 2004/0097915 A1 | 5/2004 | Refior et al. |
| 2004/0116919 A1 | 6/2004 | Heim et al. |
| 2004/0133189 A1 | 7/2004 | Sakurai |
| 2004/0138653 A1 | 7/2004 | Dabney et al. |
| 2004/0138654 A1 | 7/2004 | Goble |
| 2004/0143263 A1 | 7/2004 | Schechter et al. |
| 2004/0147918 A1 | 7/2004 | Keppel |
| 2004/0167508 A1 | 8/2004 | Wham et al. |
| 2004/0172016 A1 | 9/2004 | Bek et al. |
| 2004/0193148 A1 | 9/2004 | Wham et al. |
| 2004/0230189 A1 | 11/2004 | Keppel |
| 2004/0243120 A1 | 12/2004 | Orszulak et al. |
| 2004/0260279 A1 | 12/2004 | Goble et al. |
| 2005/0004564 A1 | 1/2005 | Wham et al. |
| 2005/0004569 A1 | 1/2005 | Witt et al. |
| 2005/0004634 A1 | 1/2005 | Ricart et al. |
| 2005/0021020 A1 | 1/2005 | Blaha |
| 2005/0021022 A1 | 1/2005 | Sturm et al. |
| 2005/0070896 A1 | 3/2005 | Daniel et al. |
| 2005/0101949 A1 | 5/2005 | Harano et al. |
| 2005/0101951 A1 | 5/2005 | Wham et al. |
| 2005/0109111 A1 | 5/2005 | Manlove et al. |
| 2005/0113818 A1 | 5/2005 | Sartor et al. |
| 2005/0113819 A1 | 5/2005 | Wham et al. |
| 2005/0149151 A1 | 7/2005 | Orszulak et al. |
| 2005/0182398 A1 | 8/2005 | Paterson |
| 2005/0197659 A1 | 9/2005 | Bahney |
| 2005/0203504 A1 | 9/2005 | Wham et al. |
| 2006/0025760 A1 | 2/2006 | Podhajsky |
| 2006/0079871 A1 | 4/2006 | Plaven et al. |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0281360 A1 | 12/2006 | Sartor et al. |
| 2006/0291178 A1 | 12/2006 | Shih |
| 2007/0038209 A1 | 2/2007 | Buysse et al. |
| 2007/0093800 A1 | 4/2007 | Wham et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2007/0173806 A1 | 7/2007 | Orszulak et al. |
| 2007/0173810 A1 | 7/2007 | Orszulak |
| 2007/0173813 A1 | 7/2007 | Odom |
| 2007/0208339 A1 | 9/2007 | Arts et al. |
| 2007/0225698 A1 | 9/2007 | Orszulak et al. |
| 2007/0250052 A1 | 10/2007 | Wham |
| 2007/0265612 A1 | 11/2007 | Behnke et al. |
| 2007/0282320 A1 | 12/2007 | Buysse et al. |
| 2008/0015563 A1 | 1/2008 | Hoey et al. |
| 2008/0015564 A1 | 1/2008 | Wham et al. |
| 2008/0039831 A1 | 2/2008 | Odom et al. |
| 2008/0039836 A1 | 2/2008 | Odom et al. |
| 2008/0082094 A1 | 4/2008 | McPherson et al. |
| 2008/0125767 A1 | 5/2008 | Blaha |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4339049 A1 | 5/1995 |
| DE | 19717411 A1 | 11/1998 |
| DE | 19848540 A1 | 5/2000 |
| EP | 246350 A1 | 11/1987 |
| EP | 310431 A2 | 4/1989 |
| EP | 325456 A2 | 7/1989 |
| EP | 336742 A2 | 10/1989 |
| EP | 390937 A1 | 10/1990 |
| EP | 556705 A1 | 8/1993 |
| EP | 569130 A1 | 11/1993 |
| EP | 608609 A2 | 8/1994 |
| EP | 694291 A1 | 1/1996 |
| EP | 836868 A2 | 4/1998 |
| EP | 878169 A1 | 11/1998 |
| EP | 880220 A2 | 11/1998 |
| EP | 0640317 B1 | 9/1999 |
| EP | 1051948 A2 | 11/2000 |
| EP | 1053720 A1 | 11/2000 |
| EP | 1151725 A1 | 11/2001 |
| EP | 1293171 A2 | 3/2003 |
| EP | 1472984 A1 | 11/2004 |
| EP | 1495712 A1 | 1/2005 |
| EP | 1500378 A1 | 1/2005 |
| EP | 1535581 A2 | 6/2005 |
| EP | 1609430 A1 | 12/2005 |
| EP | 1645235 A1 | 4/2006 |
| EP | 1707143 A1 | 10/2006 |
| EP | 1707144 A1 | 10/2006 |
| EP | 1744354 A2 | 1/2007 |
| EP | 1810628 A1 | 7/2007 |
| EP | 1810630 A1 | 7/2007 |
| EP | 1810633 A2 | 7/2007 |
| EP | 1854423 A2 | 11/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |

(56) References Cited

FOREIGN PATENT DOCUMENTS

| | | |
|---|---|---|
| FR | 2 517 953 A1 | 6/1983 |
| FR | 2 573 301 A1 | 5/1986 |
| GB | 607850 A | 9/1948 |
| GB | 702510 A | 1/1954 |
| GB | 855459 A | 11/1960 |
| GB | 902775 A | 8/1962 |
| GB | 2164473 A | 3/1986 |
| GB | 2214430 A | 9/1989 |
| GB | 2358934 A | 8/2001 |
| SU | 166452 | 1/1965 |
| SU | 727201 A2 | 4/1980 |
| WO | 9206642 A1 | 4/1992 |
| WO | 9324066 A1 | 12/1993 |
| WO | 9410922 A1 | 5/1994 |
| WO | 9424949 A1 | 11/1994 |
| WO | 9428809 A1 | 12/1994 |
| WO | 9509577 A1 | 4/1995 |
| WO | 9519148 A1 | 7/1995 |
| WO | 9525471 A2 | 9/1995 |
| WO | 96/04860 A1 | 2/1996 |
| WO | 9602180 A2 | 2/1996 |
| WO | 9608794 A1 | 3/1996 |
| WO | 9618349 A2 | 6/1996 |
| WO | 9629946 A1 | 10/1996 |
| WO | 9639086 A1 | 12/1996 |
| WO | 9639914 A1 | 12/1996 |
| WO | 9706739 A2 | 2/1997 |
| WO | 9706740 A2 | 2/1997 |
| WO | 9706855 A2 | 2/1997 |
| WO | 9711648 A2 | 4/1997 |
| WO | 9717029 A1 | 5/1997 |
| WO | 9807378 A1 | 2/1998 |
| WO | 9818395 A1 | 5/1998 |
| WO | 9827880 A1 | 7/1998 |
| WO | 9912607 A1 | 3/1999 |
| WO | 0200129 A1 | 1/2002 |
| WO | 0211634 A1 | 2/2002 |
| WO | 0245589 A2 | 6/2002 |
| WO | 0247565 A2 | 6/2002 |
| WO | 02053048 A1 | 7/2002 |
| WO | 02088128 A1 | 11/2002 |
| WO | 03090635 A1 | 11/2003 |
| WO | 03092520 A1 | 11/2003 |
| WO | 2003090630 A2 | 11/2003 |
| WO | 2004028385 A1 | 4/2004 |
| WO | 2004043240 A2 | 5/2004 |
| WO | 2004052182 A2 | 6/2004 |
| WO | 2004098385 A2 | 11/2004 |
| WO | 2004/103156 A2 | 12/2004 |
| WO | 2005046496 A1 | 5/2005 |
| WO | 2005048809 A1 | 6/2005 |
| WO | 2005050151 A1 | 6/2005 |
| WO | 2005060365 A2 | 7/2005 |
| WO | 2005060849 A1 | 7/2005 |
| WO | 2006050888 A1 | 5/2006 |
| WO | 2006105121 A2 | 10/2006 |

OTHER PUBLICATIONS

International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
Muller et al., "Extended Left Hemicolectomy Using the LigaSure Vessel Sealing System" Innovations That Work; Sep. 1999.
International Search Report EP 06010499.9 dated Jan. 29, 2008.
International Search Report EP 07001489.9 dated Dec. 20, 2007.
International Search Report EP 07001491 dated Jun. 6, 2007.
International Search Report EP 07009322.4 dated Jan. 14, 2008.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP07001494.9 dated Aug. 12, 2010.
Extended European Search Report from corresponding European Patent Application No. 07001494.9 dated Mar. 7, 2011.
Examiner's First Report issued in the corresponding Australian Application No. 2007200292 dated Dec. 9, 2011.
Alexander et al., "Magnetic Resonance Image-Directed Stereotactic Neurosurgery: Use of Image Fusion with aomputerized Tomography to EnhanceSpatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-Iridium Interstitial Implants" Medical Physics, 9 (3), May/Jun. 1982.
Bergdahl et al., "Studies on Coagulation and the Development of an Automatic Computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B. V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Bosman et al., "Radiofrequency Lesion Generation and Its Effect on Tissue Impedance" Applied Neurophysiology 51: (1988) pp. 230-242.
Bosman et al., "Theoretical Aspects of Radiofrequency Lesions in the Dorsal Root Entry Zone" Neurosurgery 15: (1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure The O.R. Pro 300 1 p. Sep. 1998.
Ogden Goertzel Alternative to the Fourier Transform: Jun. 1993 pp. 485-487 Electronics World; Reed Business Publishing, Sutton, Surrey, BG vol. 99, No. 9. 1687.
Sugita et al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp. Nov. 1995.
Vallfors et al., "Automatically Controlled Bipolar Electrosoagulation—'COA-COMP'" Neurosurgical Review 7:2-3 (1984) pp. 187-190.
Wald et al., "Accidental Burns", JAMA, Aug. 16, 1971, vol. 217, No. 7, pp. 916-921.
Richard Wolf Medical Instruments Corp. Brochure, "Kleppinger Bipolar Forceps & Bipolar Generator" 3 pp. Jan. 1989.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 05002769.7 dated Jun. 9, 2006.
International Search Report EP 06000708.5 dated Apr. 21, 2006.
International Search Report—extended EP 06000708.5 dated Aug. 22, 2006.

(56) References Cited

OTHER PUBLICATIONS

International Search Report EP 06006717.0 dated Aug. 7, 2006.
International Search Report EP 07008207.8; dated Sep. 5, 2007.
International Search Report EP 07010673.7; dated Sep. 24, 2007.
U.S. Pat. No. 6,878,148, Apr. 2005, Goble et al. (withdrawn).
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
International Search Report EP04707738 dated Jul. 4, 2007.
International Search Report EP08004667.5 dated Jun. 3, 2008.
International Search Report EP08006733.3 dated Jul. 28, 2008.

\* cited by examiner

METHOD AND SYSTEM FOR CONTROLLING AN OUTPUT OF A RADIO-FREQUENCY MEDICAL GENERATOR HAVING AN IMPEDANCE BASED CONTROL ALGORITHM

CROSS REFERENCE TO RELATED PATENT APPLICATIONS

This application is a continuation application of U.S. patent application Ser. No. 14/192,112, now U.S. Pat. No. 9,642,665, filed on Feb. 27, 2014, which is a continuation application of U.S. patent application Ser. No. 11/657,173, now U.S. Pat. No. 8,663,214, filed on Jan. 24, 2007, which claims priority to U.S. Provisional Application Ser. No. 60/761,498 filed on Jan. 24, 2006, the entire contents of each of which are incorporated by reference herein.

BACKGROUND

The present disclosure is directed to electrosurgery and, in particular, to a control system for an electrosurgical generator. The control system has a control algorithm that continually adjusts for changes in initial tissue conditions to enhance tissue fusion.

TECHNICAL FIELD

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by an electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., veins and/or soft tissue structures, such as lung, brain and intestine. A surgeon can cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electro-diathermy"). The term "coagulation" is defined as a process of desiccating tissue wherein the tissue cells are ruptured and dried.

"Vessel sealing" or "tissue fusion" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them while larger vessels or tissue need to be sealed to assure permanent closure. It has been known that different waveforms of electrosurgical energy are suited for different surgical affects, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform is desired.

In order to optimize sealing or tissue fusion without causing unwanted charring of tissue at the surgical site or possibly causing collateral damage to adjacent tissue, e.g., thermal spread, it is necessary to control the output from the electrosurgical generator, e.g., power, waveform, voltage, current, pulse rate, etc.

It is known that measuring the electrical impedance and change thereof across the tissue at the surgical site provides a good indication of the state of desiccation or drying of the tissue during the tissue fusion or vessel sealing process. It has been observed that as the tissue dries or loses moisture, the impedance across the tissue rises. This observation has been utilized in some electrosurgical generators to regulate the electrosurgical power based on a measurement of tissue impedance. For example, commonly owned U.S. Pat. No. 6,210,403 relates to a system and method for automatically measuring the tissue impedance and altering the output of the electrosurgical generator. The alteration is based on the measured impedance across the tissue. The content of this patent is hereby incorporated by reference in its entirety.

The supply of energy may also be controlled such that it is supplied in a continuous fashion to seal vessels tissue wherein the input/output is responsive to tissue hydration/volume through feedback control. Delivery of the electrosurgical energy in pulses allows the tissue to cool between pulses. The pulses also allow some moisture to return to the tissue between pulses which is known to enhance the sealing process.

It is further known to clamp or clip excess voltage output from the electrosurgical generator by the use of avalanche devices, such as diodes, zener diodes and other devices, resulting in absorption and dissipation of excess energy in the form of heat.

Commonly owned U.S. Pat. No. 6,398,779 discloses a sensor which measures the initial tissue impedance with a calibrating pulse which, in turn, sets various electrical parameters based on a look-up table stored in a computer database. The transient pulse width associated with each pulse measured during activation is used to set the duty cycle and amplitude of the next pulse. Generation of electrosurgical power is automatically terminated based on a predetermined value of the tissue impedance across the tissue.

One significant aspect of such prior art electrosurgical generators is that often such generators use software which provides for an initial reading of one or more parameters of the tissue. However, such an initial tissue reading may be a so called "false" reading depending on the initial positioning or disposition of the electrode. The false reading may be input into the control algorithm of the electrosurgical generator which compensates for the false reading. It would be advantageous to provide a control for an electrosurgical generator which both disregards such initial, not reliable, readings where the tissue does not react and distinguishes a "false" reading from a "true" reliable reading.

Thus, a need exists to develop an electrosurgical generator which includes improved control circuitry for processing an impedance of the tissue over time and for providing continuous control of various electrical parameters (e.g., pulse frequency and intensity, voltage, current, power) of the electrosurgical generator based upon continually sensed information from the surgical site. In addition, a need exists to develop control circuitry which is designed to disregard initial readings sensed from the surgical site where no reaction with the tissue occurs.

SUMMARY

It is an object of the present disclosure to provide a system having a control module and a sensor that determines and continually monitors whether a tissue reacts to an electrode by sensing and recording a change in impedance over time.

It is an object of the present disclosure to provide for a system having a control module and a sensor that determines whether a tissue reacts to an electrode by sensing a change in the impedance per unit time and, in response to a determination that the tissue has reacted, the control module enters into an energy control mode.

It is another object of the present disclosure to provide for a system having a control module and a sensor that monitors a parameter and in response to the parameter provides a predetermined amount of current per unit time in order to prevent a rapid and uneven vaporization of liquid and fluid in the tissue with the predetermined amount of current per unit time being complementary to the monitored parameter.

It is still another object of the present disclosure to provide for a system that has a control module with a sensor that monitors a change in an impedance per unit time to determine a stability of a tissue reaction with an electrode.

It is yet another object of the present disclosure to provide for a system having a control module and a sensor that monitors a parameter and stores the parameter in a memory over time and in response to the stored parameter provides a predetermined amount of current per unit time to prevent a rapid and uneven vaporization of liquid and fluid in the tissue with the predetermined amount of current per unit time being complementary to a measurement from the stored parameter.

According to a first aspect of the present disclosure, a system for performing an electrosurgical procedure at a surgical site is disclosed. The system includes a sensor configured to continually sense an electrical and/or a physical property of tissue at a surgical site and to generate a sensor signal as a function thereof. The system also includes a control module configured to process the sensor signal using a processor, an algorithm, and a map having one or more predetermined values. The control module is further configured to compare the sensor signal to a predetermined level to determine reliability of the sensor signal and to signal an electrosurgical generator in response to a reliable sensor signal such that the electrosurgical generator enters energy control mode, wherein the electrosurgical generator matches an output of the control signal with a predetermined value from the map.

A method for performing an electrosurgical procedure at a surgical site is also contemplated by the present disclosure. The method includes the steps of continually sensing electrical and physical properties of the surgical site and generating a sensor signal as a function thereof and processing the sensor signal using a processor, an algorithm, and a map having one or more values to verify a reactance of tissue at the surgical site. The method also includes the step of entering an energy control mode, wherein the electrosurgical generator matches an output of the control signal with a value from the map, based on the determination of the reactance of tissue in the processing step.

According to another aspect of the present disclosure, a system for performing an electrosurgical procedure at a surgical site is disclosed. The system includes a sensor configured to continually sense an electrical and/or physical property of the surgical site and to generate a sensor signal as a function thereof. The system also includes a control module configured to process the sensor signal using a processor, an algorithm, and a map having one or more values. The control module is further configured to verify tissue reactance and to signal an electrosurgical generator based on the verification of tissue reactance such that the electrosurgical generator enters energy control mode. The electrosurgical generator matches an output of the control signal with a value from the map, wherein the control module is configured to recalculate the map when tissue impedance increases above a predetermined threshold and to signal the electrosurgical generator to renter energy control mode.

BRIEF DESCRIPTION OF THE DRAWINGS

Various embodiments will be described herein below with reference to the drawings wherein.

DETAILED DESCRIPTION

Figure 1:
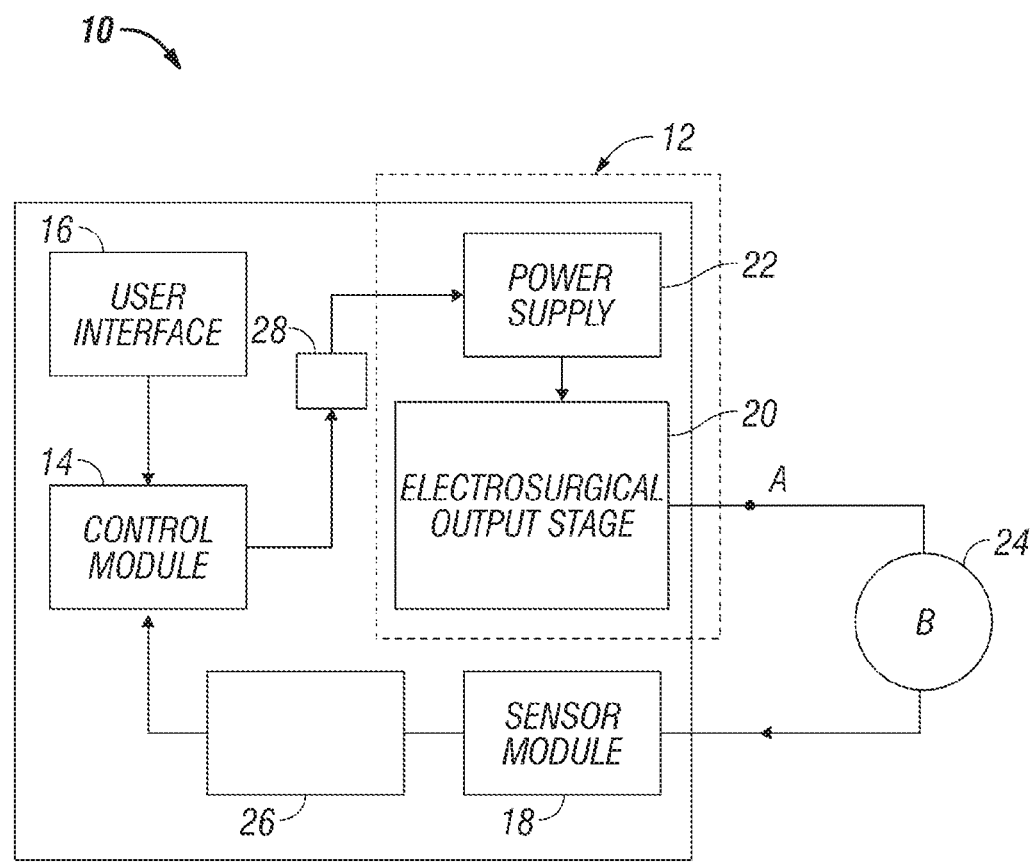
FIG. 1 is a schematic diagram of a control system for use with an electrosurgical generator according to the present disclosure.

Reference should be made to the drawings where like reference numerals refer to similar elements throughout the various figures.

Referring to FIG. 1, there is shown a schematic diagram of one embodiment of the presently disclosed closed loop control system 10 for use with an electrosurgical generator 12. Control system 10 includes a control module 14, user interface 16 and sensor module 18. The control module 14 is operatively connected to the electrosurgical generator 12.

The control module 14 includes program instructions to detect a specified increase in a parameter at an initial time of operation to determine whether a reaction of the tissue has occurred. If no tissue reaction occurs, the control module 14 compensates and prevents initial data from entering a control algorithm. This initial data is considered to be unreliable. The parameter may be any parameter capable of being measured by the sensor module 18 of operation or calculated from data provided by the sensor module by the control module 14. In one embodiment, the parameter is a change in tissue impedance over time.

If a tissue reaction occurs and is detected, this data is considered to be reliable and the control module 14 enters an energy control mode. The energy control mode regulates electrosurgical generator 12 to output RF energy that matches a monitored tissue impedance parameter with a preset slope trajectory. The preset slope trajectory may be derived from a number of stored parameters or alternatively may be derived from a desired output or a desired effect. The preset slope trajectory is from a stored value in a map or memory and is intended to output RF energy to produce an optimal tissue seal. The stored values may be obtained by accessing a stored mapping of continuous values or alternatively a table or equivalent.

The electrosurgical generator 12 includes electrosurgical energy output stage 20 and a power supply 22. The electrosurgical output stage 20 receives power from the power supply 22 and delivers RF energy to a patient 24 via at least one electrode (not explicitly shown). As can be appreciated, one or more electrodes may be used with the electrosurgical instrument for performing monopolar or bipolar surgery.

The sensor module 18 senses various electrical and physical parameters or properties at the operating site and communicates with the control module 14. In response, the control module 14 regulates the electrosurgical output from the output stage 20. The sensor module 18 may be configured to measure or "sense" one or more various electrical or electromechanical conditions at the operating site, including but not limited to, tissue impedance, changes in tissue impedance, tissue temperature, changes in tissue temperature, leakage current, applied voltage and applied current, and other parameters.

The sensor module 18 is configured to measure one or more of these conditions continuously or in "real time". The sensor module 18 measures the conditions such that the control module 14 can continually modulate the electrosurgical output according to a specific purpose or desired surgical intent. More particularly, analog signals provided by the sensor module 18 are converted to digital signals via an analog-to-digital converter (ADC) 26. The digital signals are then provided to the control module 14.

The control module 14, thereafter, regulates the power supply 22 and/or the electrosurgical output stage 20 according to the information obtained from the sensor module 18.

The user interface 16 is electrically connected to the control module 14 to allow the user to control various parameters of the electrosurgical energy output to the patient 24 during surgery to manually set, regulate and/or control one or more electrical parameters of the delivered RF energy. Such parameters may include but are not limited to voltage, current, power, frequency, amplified, and/or pulse parameters such as a pulse width, a duty cycle, a crest factor, and/or a repetition rate depending upon a particular purpose or to change surgical intent.

The control module 14 includes at least one microprocessor capable of executing software instructions for processing data received by the user interface 16 and the sensor module 18. The control module 14 outputs control signals to the electrosurgical output stage 20 and/or the power supply 22, accordingly. The software instructions (executable by the control module) are stored in an internal memory in the control module 14, an internal or external memory bank accessible by the control module and/or an external memory, e.g., an external hard drive, floppy diskette, CD-ROM, etc. or any other recordable medium. Control signals from the control module 14 to the electrosurgical generator 12 may be converted to analog signals by a digital-to-analog converter 28.

The power supply 22 is a high voltage DC power supply for producing electrosurgical current, e.g., radiofrequency (RF) current. Signals received from the control module 14 control the magnitude of the voltage and current output by the DC power supply. The electrosurgical output stage 20 receives the output current from the DC power supply and generates one or more pulses or a continuous sinusoidal waveform via a waveform generator (not explicitly shown).

The pulse parameters, such as pulse width, duty cycle, crest factor and repetition rate are regulated in response to the signals received from the control module 14. Alternatively, the power supply 22 may be an AC power supply, and the electrosurgical output stage 20 may vary the waveform of the signal received from power supply 22 to achieve a desired waveform.

The user interface 16 may be local to, adjacent to, or remote from the control module 14. A user may enter data such as the type of electrosurgical instrument being used, the type of electrosurgical procedure to be performed, and/or the tissue type upon which the electrosurgical procedure is being performed. The generator 12 may also be configured to recognize one or more parameters automatically, e.g., based on the type of the electrosurgical instrument being used.

The closed loop control system 10, in particular the sensor module 18, may include one or more smart sensors. The sensors provide feedback to the surgeon relating to one or more of these physical parameters. Furthermore, the user may enter commands, such as a target effective voltage, current or power level to be maintained, or a target response, e.g., change in regulation of the power supply 22 and/or electrosurgical output stage 20, to changes in sensed values, such as an effective change in voltage, current and/or power level as a function of the changes. The user may also enter commands for controlling electrical parameters of the RF energy, delivered by the electrosurgical generator 12, as described above. A default value is provided for the above target levels and target responses.

The sensor module 18 includes a number of sensors (not explicitly shown) strategically located for sensing various properties or conditions at or proximate points "A" and "B" as shown in FIG. 1. Sensors positioned at or proximate point "A" (hereinafter referred to as at point "A") sense one or more properties and/or parameters of electrosurgical output from electrosurgical output stage 20, and/or properties, parameters or conditions prior to surgical effect of the currently administered electrosurgical energy during the surgical procedure. Sensors positioned at point "A" may be provided with or attached proximate the generator 12.

Sensors (not explicitly shown) positioned at or proximate point "B" (hereinafter referred to as at point "B") sense one or more parameters, properties and/or conditions at or across the operating site prior to the surgical procedure and/or in response to surgical effect during the surgical procedure and these sensors may be included with the electrosurgical instrument (e.g., on one end or opposing end effectors) or attached proximate the operating site. In one embodiment, optical sensors, proximity sensors, temperature sensors may be used to detect certain tissue characteristics, and electrical sensors may be employed to sense other parameters of the tissue or operating effects. Point "A" may be proximate the surgical site "B" at a location where the signals outputted by the generator 12 are propagated before they are applied or approximately when they are applied to the surgical site "B".

The sensors are provided with leads or possibly a suitable wireless device for transmitting information to the control module 14. The information may be provided directly to the control module and/or provided to the control module via the sensor module 18 and/or the analog to digital converter 26. The sensor module 18 may also have a device for receiving information from multiple sensors. The sensor module 18 may provide the information and the source of the information (e.g., the particular sensor providing the information) to the control module 14.

Figure 2:
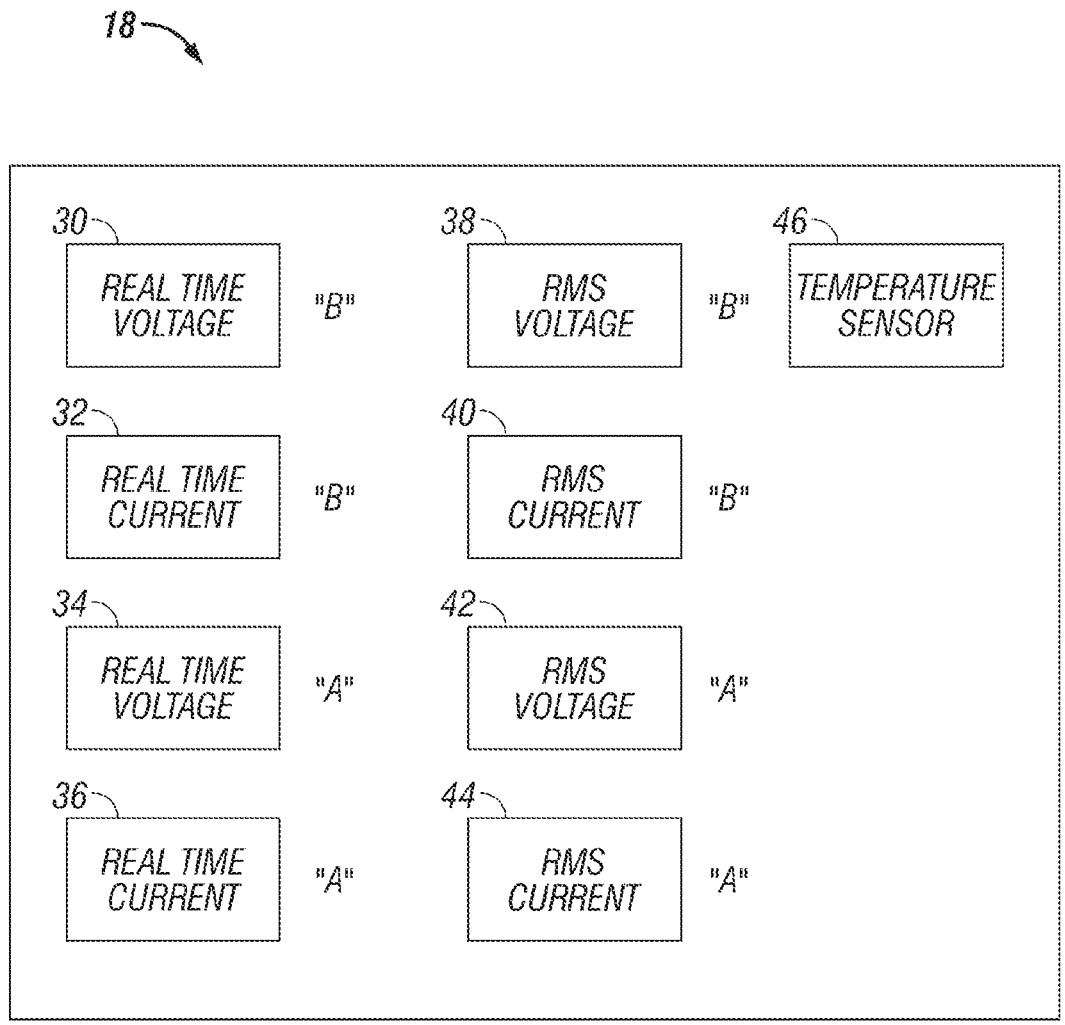
FIG. 2 is a schematic diagram of a sensor module for use with the control system of FIG. 1.

Referring now to FIG. 2, there is shown a block diagram of the sensor module 18. The sensor module 18 has a real-time voltage sensing system 30 and a real-time current sensing system 32 for sensing real-time values for applied voltage and current at the surgical site "B". The sensor module 18 also has a real-time voltage sensing system 34 and a real-time current sensing system 36 for sensing real-time values of signals returned from the patient at a point "A".

The sensor module 18 further has an RMS voltage sensing system 38 and an RMS current sensing system 40 are also included for sensing and deriving RMS values for applied voltage and current at the surgical site "B". An RMS voltage sensing system 42 and an RMS current sensing system 44 are included for sensing and deriving RMS values of signals at point "A". The sensor module 18 also has a temperature sensing system 46. The temperature sensing system 46 is included for sensing tissue temperature at the surgical site "B".

Real-time and RMS current and voltage sensing systems are known in the art. The sensor module 110 may further include other sensors (not explicitly shown) for sensing voltage and current output by the generator.

The measured or sensed values are further processed, either by circuitry and/or a processor (not explicitly shown) in the sensor module 18 and/or by the control module 14, for deriving changes in sensed values and tissue impedance at the surgical site "B".

Tissue impedance and changes in tissue impedance may be determined in one embodiment by measuring the voltage and/or current across the tissue and/or calculating changes thereof over time, and comparing the voltage and current values to known and/or desired values associated with various tissue types for use by the control system 10 to drive electrical output to achieve desired impedance and/or change in impedance values.

As can be appreciated, these known and/or desired values, tissue types and ranges may be stored in an internal look-up table, "a continuous value map" or in an external searchable memory. Commonly owned U.S. Pat. Nos. 6,398,779, 6,203,541, 5,827,271 and U.S. patent application Ser. No. 10/073,761 disclose methods for measuring tissue impedance, and are all incorporated by reference herein in their entirety.

By deriving tissue impedance (or other physical and electrical parameters) from real-time value(s) provides the benefit of monitoring real-time tissue impedance and/or changes in tissue impedance. As the surgical procedure proceeds, it is believed that the tissue impedance fluctuates in response to removal and restoration of liquids from the tissue at the surgical site "B". As the control module 14 monitors the tissue impedance and changes in tissue impedance (or other physical and electrical parameters) the control module regulates the power supply 22 and electrosurgical output stage 20 accordingly for achieving the desired and optimal electrosurgical effect. Such a system is described in United States Published Patent Application Number US 2004/0015163 A1 to Buysse, et al. which is herein incorporated by reference in its entirety.

Before beginning an electrosurgical procedure, an operator of the electrosurgical instrument enters information via the user interface 16. Information entered includes, for example, the type of electrosurgical instrument being used, the type of procedure being performed (i.e., desired surgical effect), the type of tissue, relevant patient information, and a control mode setting. The control mode setting determines the amount of or type of control that the control module 14 will provide. The one or more sensors (not explicitly shown) may also be included to automatically provide information to the control module 14 relating to tissue type, initial tissue thickness, initial tissue impedance, etc.

The modes include, but are not limited to, one or a combination of one or more of the following modes: a first mode, a second mode, a third mode or any number of modes. The first mode is defined as the stage when the control module 14 maintains a steady selected output power, current and/or voltage value at site "A".

The second mode is defined as the stage when the control module 14 maintains a steady selected output power, current and/or voltage value at site "B". The third mode is defined as the stage when the control module 14 maintains a variable selected output power, current and/or voltage values at site "A" which is dependent upon (i.e., a function of) time value(s) and/or sensed parameter(s) or changes in sensed parameter(s) during the procedure. The fourth mode is defined as the stage when the control module 14 maintains a variable selected output power, current and/or voltage values at site "B", which is dependent upon (i.e., a function of) time value(s) and/or sensed parameter(s) or changes in sensed parameter(s) during the procedure.

Functions performed on the time value(s) and sensed properties(s) include operations such as calculations and/or look-up operations using a table or map stored by or accessible by the control module 14. The control module 14 processes the selected output power, current and voltage values, such as by performing calculations or table look up operations from a database, to determine power control signal values and output control values.

The control module 14 determines an initial setting for control signals to the power supply 22 and the output stage 20 by using and/or processing operator-entered data or settings, performing calculations and/or accessing a look-up table stored by or accessible by the control module 14.

Once the electrosurgical procedure begins, the sensors 30 through 46 of sensor module 18 sense various physical and electrical properties and provide feedback to the control module 14 through the converter 26. The control module 14 processes the feedback information in accordance with the pre selected mode, as well as any additional operator-entered commands entered during the procedure. The control module 14 then sends control information to the power supply 22 and the output stage 20. The electrosurgical generator 12 may be provided with override controls, to allow the operator to override the control signals provided by the control module 14, if needed, e.g., by entering override commands via the user interface 16 or at any other suitable location.

The electrical impedance and change thereof across the tissue at the surgical site indicated on FIG. 1 as reference letter "B" provides a favorable indication of the state of desiccation or drying of the tissue. As the tissue dries or looses moisture, the impedance across the tissue rises. This observation has been used in some electrosurgical generators to regulate the electrosurgical power based on a measurement of tissue impedance. For example, commonly owned U.S. Pat. No. 6,210,403 which is herein incorporated by reference relates to a system and method for automatically measuring the tissue impedance and altering the output of the electrosurgical generator based on the measured impedance across the tissue.

As the impedance of the tissue changes the current changes inversely proportionally if the voltage remains constant. This is basically defined by Ohm's law wherein, $V=IR$ wherein V is the voltage, I is the current, and I is the current along the electrode in milliamps. When the tissue impedance increases, the current will decrease. If the tissue impedance decreases, the current will increase. Increases/decreases in the current may be detector by the sensor module 18.

Figure 3:
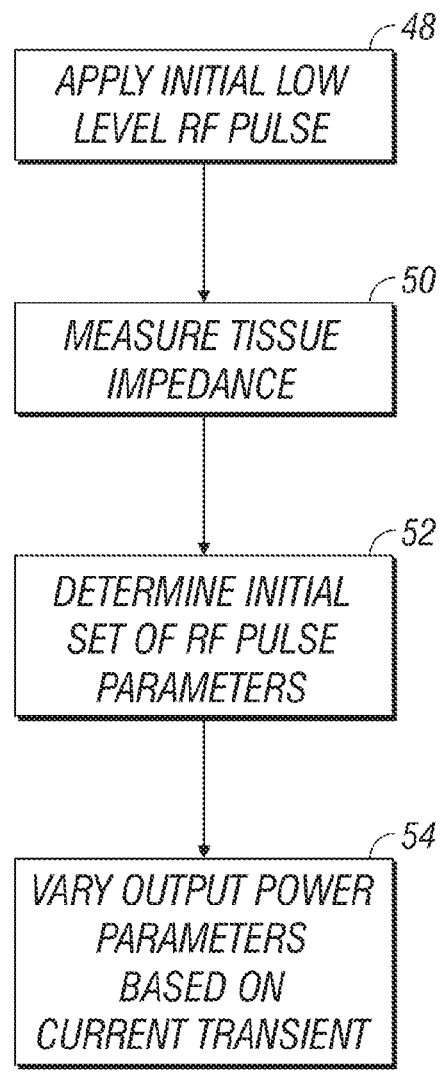
FIG. 3 is a flowchart illustrating a method of operation of the control system according to one aspect of the present disclosure.

Referring now to FIG. 3, there is shown a general basic block diagram of a software algorithm that is executed by the control module 14. The control module 14 controls one of or both of the power supply 22 and/or the electrosurgical output stage 20 and at step 48, the control module 14 controls the power supply and/or the electrosurgical output stage to emit a low power initial pulse of RF energy. The pulse is used to sense at least one electrical characteristic of the tissue.

Next, the sensor module 18 communicates the data to the converter 26 and the converter communicates a digital signal to the control module 14. The control module 14 measures tissue impedance or another electrical characteristic shown as step 50. Thereafter, the control module 14 uses the sensed electrical characteristic of the tissue as an input into the determination of the initial radio frequency parameters shown as step 52. At step 54, the control module 14 may vary the output power parameters based in part on the current transient or in this instance using the impedance, as described in commonly-owned U.S. Pat. No. 6,398,779, the contents of which are hereby incorporated by reference in its entirety.

Figure 4:
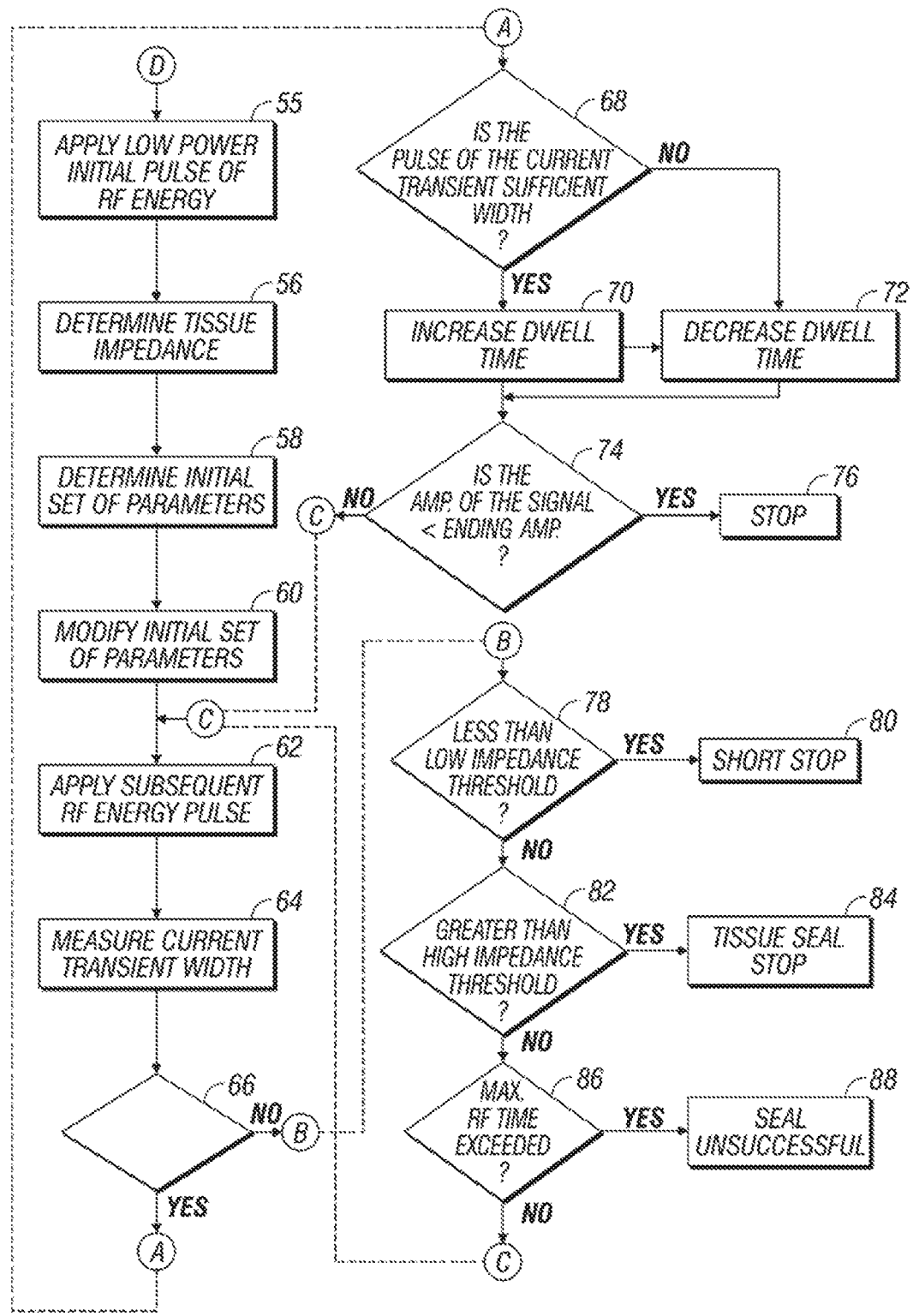
FIG. 4 is another flowchart illustrating a method of operation of the control system according to the present disclosure.

Referring now also to the logic flow diagram of FIG. 4, the impedance sensing feature is implemented at the beginning of a cycle, for example, a vessel seal cycle or another surgical cycle. One skilled in the art should appreciate that the cycle may be any electrosurgical surgical operation known in the art. The electrosurgical generator 10 senses at least one electrical characteristic of the tissue, for example, impedance, I-V phase rotation, or the output current, by using a short burst of RF energy shown as step 55. The electrical characteristic of the tissue such as the tissue impedance may be measured at any frequency or power level, but is performed at the same frequency as the intended working frequency (e.g., 470 kHz). A short burst of RF energy from the electrosurgical output stage 20 (less than about 200 milliseconds, and about 100 milliseconds) is a 470 kHz sine wave with approximately 5 W of power. However, one skilled in the art should appreciate that other configurations are also possible.

The initial pulse RF power is made low at step 55, and the pulse time is made as short as possible, to enable an initial tissue electrical characteristic measurement to be made such as the tissue impedance without excessively heating the tissue at step 56. Next, the control module 14 using the tissue impedance or another electrical characteristic determines the initial set of output power parameters shown as step 58. Some of the values that are obtained include power, maximum voltage, starting voltage, minimum voltage, voltage decay, voltage ramp, maximum RF on time, maximum cool scale factor, pulse minimum, pulse dwell time, pulse off time, and the pulse desired width.

The control module 14 then modifies the initial set of parameters per seal intensity control input shown as step 60 and applies a subsequent RF energy pulse shown as step 62 and a measure of the current transient pulse width is made at step 64.

A determination is made at step 66 by the control module 14. The determination is whether there is a current transient is present or whether there is a short lived oscillation between the first pulse and a successive pulse caused by one or more parameters such as the tissue impedance, change in voltage or current load. If there is a current transient present, the control is passed to step 68 as indicated by the broken line in FIG. 4. If there is not a current transient present, the control is passed to step 78 as shown by the broken line in FIG. 4.

At step 68, a determination is made as to whether the pulse of the current transient is sufficiently wide. If the pulse is sufficiently wide or in the range of 500 to 1000 ms, then the control module 14 assumes a presence of a large amount of tissue, or that the selected tissue requires more RF energy to desiccate. If sufficiently wide, the control passes to step 70. If not sufficiently wide, the control passes to step 72.

At step 70, the dwell time is increased and a reduction of amplitude is made of the next RF pulse. If the pulse of the current transient is not sufficiently wide or is narrow, for example about 250 ms or less, then the control module 14 can assume a small amount of tissue, or a tissue type that requires little RF energy is present. The dwell time may be shortened and a reduction in the amplitude of the delay time of the next RF pulse can be made at step 72.

A decision is made at step 74 as to whether the amplitude of the signal is less than the ending amplitude. If the determination at step 74 is affirmative then the control module 14 stops the signal being emitted from the electrosurgical output stage 20 at step 76. The signal is terminated because the operation is complete and the tissue has been sealed.

If the decision at step 74 is at the negative, control passes to step 62 and the subsequent RF energy pulse is applied. If the electrical transient is not present at the determination block 66 then control passes to step 78. At step 78, given a negative output from the determination block at step 66, the tissue has either not yet begun to desiccate, a short in the system has occurred, or the seal cycle is complete. At step 78, if the impedance is less than a low impedance value, the control module 14 will assume that a shorted electrode or instrument has occurred at step 80 and terminate operation thereof.

At step 78 if the low impedance threshold has not occurred, then control passes to decision block 82. At decision block 82, if the measured impedance is greater than a predetermined high impedance threshold value, then the control passes to step 84. At step 84, control module 14 assumes that the tissue seal has been achieved and will terminate operation.

At decision block 82, if the measured impedance is not greater than a predetermined high impedance threshold value, the control passes to step 86.

At step 86, if the tissue impedance is found to be between the low impedance and the high impedance values, then control passes to a determination of whether a maximum amount of RF time has been exceeded. If this decision at step 86 is in the affirmative, the control module 14 assumes that the seal has not been made for a reason. Control will pass to step 88 and the operation is terminated for reason that the tissue seal has been assumed to be unsuccessful. Alternatively, if the maximum amount of time is not exceeded then the controller assumes that the tissue has not yet received enough RF energy to start desiccation. If the maximum amount of time is not exceeded, control passes to step 62 as indicated by a dotted line for further operation.

The initial conditions of the tissue seal or the initial conditions of touching the applicator with the electrode and applying the RF energy to the tissue are significant. Generally existing generators at step 58 of FIG. 4 will operate as follows: if the starting range was in a lower or low range, the initial power is made lower. Also, generally, if the sensed impedance was high or in a higher range, the initial power and starting voltage is made higher. The initial parameters may be obtained by the control module 14 shown in FIG. 1 by viewing a parameter lookup table. However, for an optimal tissue seal to occur, it is desirable to modulate and control the vaporization rate of fluids in the tissue. If the fluid in the tissue is heated in an uneven manner or in a manner that is too rapid, the fluid or liquid in the tissue will rapidly heat per unit time by the RF energy to expand and quickly traverse out of the tissue.

This "pop" or fluid rapidly escaping the tissue per unit time is disfavored for an optimal tissue seal condition. Thus, it is desirable to identify the initial point of fluid vaporization by the RF energy to modulate and decrease the amount of RF energy from either the electrosurgical output stage 20 or the power supply 22 to prevent such a rapid fluid vaporization for an ideal tissue seal and for a more productive initial operation of the electrosurgical generator 12, particularly at step 55 through 58 of FIG. 4.

Figure 5:
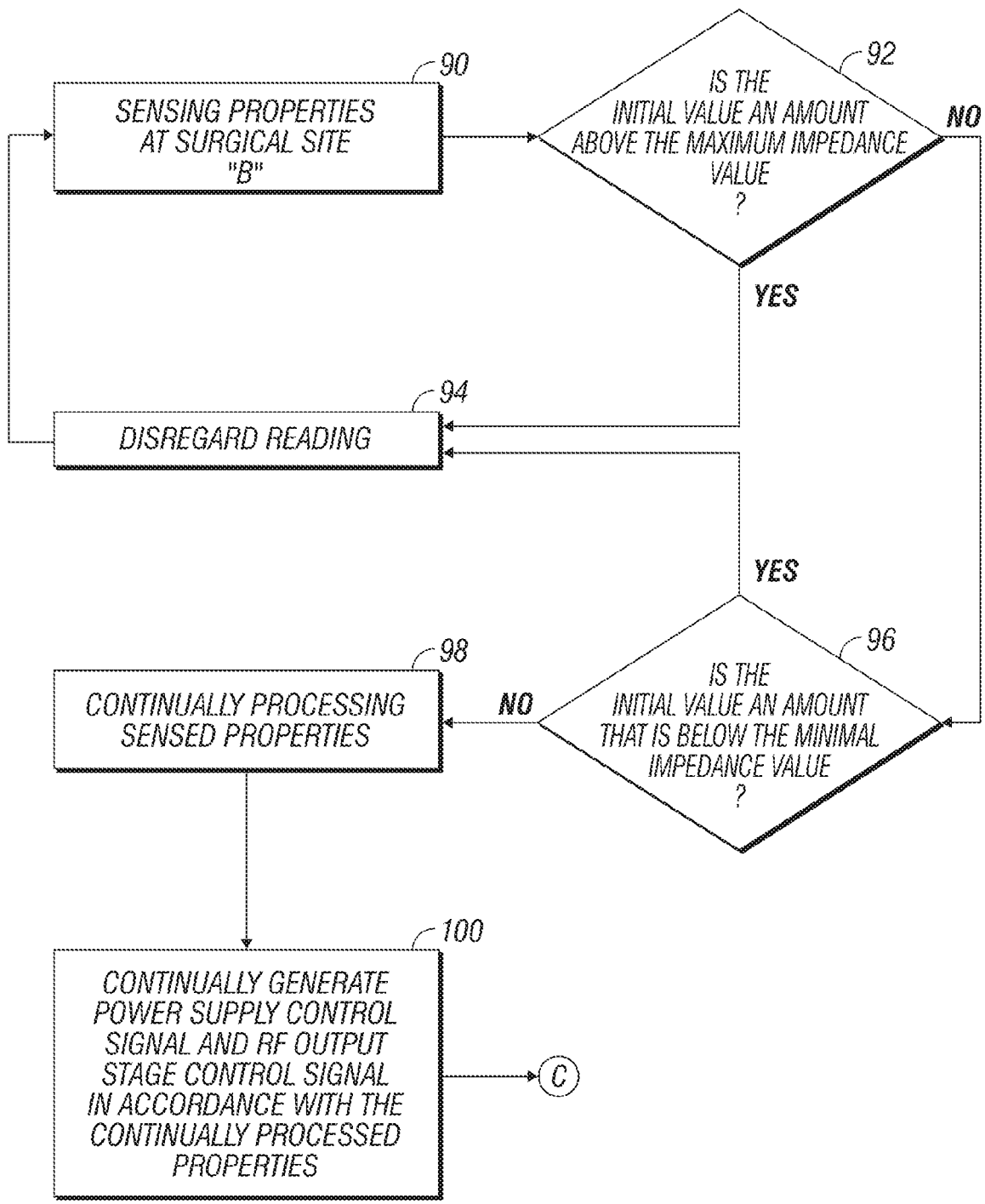
FIG. 5 is another flowchart illustrating an initial method of operation of the control system according to another aspect of the present disclosure.

Referring now to FIG. 5, the control module 14 further has a software algorithm to control either the power supply 22 and/or the electrosurgical output stage 20 in response to an initial tissue impedance reading or reaction. The software algorithm of FIG. 5 determines, by sensing one or more parameters, whether a tissue reactance occurs. When the electrode or applicator is placed on the tissue at the surgical site "B" (shown on FIG. 1), and RF energy is pulsed from the applicator, an initial reading is taken and a property or parameter such as tissue impedance is sensed by the sensor module 18 at step 90. One skilled in the art should appreciate that various parameters can be sensed by the sensor module 18 such as a control variable, an energy, a temperature, a current, or other previously mentioned parameters that are all within the scope of the present disclosure.

Control is passed to a decision block 92. At the decision block 92, a determination is made. The determination is as to whether the initial reading has a parameter such as an impedance that rises or falls above some predetermined threshold. If the initial reading has an impedance value that is above, or below a predetermined threshold then the reading is disregarded. The "false" tissue impedance reading thus is not allowed to cycle through the algorithm of the control module 14. Instead, the control is passed to step 94 to disregard the initial reading and then return to step 90 to continue sensing the impedance at surgical site "B" to allow for tissue impedance readings to cycle through the algorithm of the control module but only after a tissue reactance is determined.

Referring again to FIG. 5, there is shown the logic flow diagram of an initial cycle. The initial impedance reading of step 90 is output to decision block 92. At decision block 92, if the sensed impedance value is a predetermined amount above the maximum impedance value that is a preset maximum impedance value threshold, a decision is made at step 92. If the decision is in the affirmative, then the tissue impedance reading is disregarded at step 94. Thereafter, the cycle is continued with the RF energy being regulated at the electrosurgical stage output 20 and being output at a low power initial pulse of RF energy level.

If the decision is in the negative at step 92, control is passed to decision block 96. At decision block 96, if the sensed impedance value is an amount that is below the minimal impedance value or a preset minimal impedance value threshold, a decision is made at step 96.

If the decision is in the affirmative, then the control module 14 assumes that a tissue reactance has not occurred and the reading is disregarded at step 94, and operation is continued with the energy regulated at the electrosurgical stage output 20 and being output at an energy level that is a low power initial pulse of RF energy for sensing the properties at the surgical site "B" at step 90.

If the level is between the preset maximum impedance value threshold and the preset minimum impedance value threshold then operation continued to step 98 and the sensor module 18 senses parameters including impedance and the control module 14 continually processes sensed properties at step 98. The control then passes to step 100 to continually generate a power supply control signal and RF output in accordance, for example, with a predetermined curve based on power, impedance, current voltage, etc.

Figure 6:
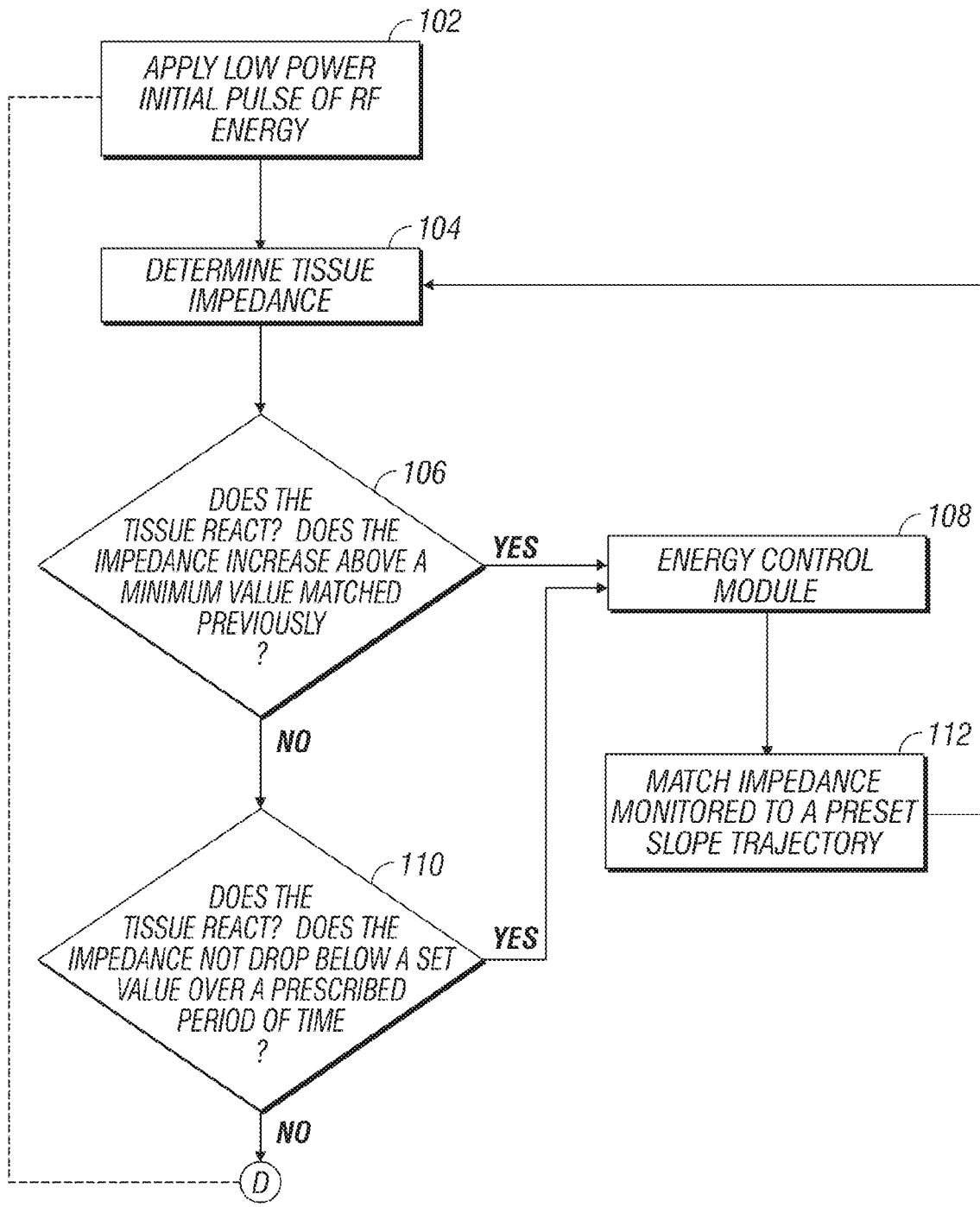
FIG. 6 is a flowchart illustrating a method of operation of the control system with an energy control mode according to another aspect of the present disclosure.

Referring now to another logic flow diagram as FIG. 6, the algorithm also has an energy control mode that supplies energy to the applicator or electrode to prevent vaporizing the fluids in the tissue. Referring now to FIG. 6, step 102 indicates to apply a low power initial pulse of RF energy to the tissue. Parameters are detected by the sensor module 18, and the control module 14 determines the tissue impedance or another parameter from the sensed parameters in step 104. Here, a reliable parameter may be stored in memory. Thereafter, control will pass to decision block 106.

At decision block 106, a decision is made as to whether the tissue reacts in response to the RF energy received. If so, the algorithm provides for an energy control mode to avoid any "pop" effect by the electrode applying RF energy to the tissue. The reaction is defined by a specified increase in impedance above a minimum value reached previously. The specified increase in impedance is loaded by the control module 14 based on tissue type and/or properties as well as electrosurgical instruments being utilized. The minimum value reached previously is obtained by the control module 14 by accessing a stored map of continuous values, or alternatively, of a table or equivalent. If the tissue does react by indicating that the impedance is a specified increase above the minimum value reached previously, the electrosurgical generator 12 passes control to step 108 and the generator enters an energy control mode. If the tissue does not react at step 106, the control passes to step 110.

At step 110, another decision is made as to whether the tissue reacts in response to the RF energy received. Here, the tissue reaction is defined by a specified drop or decrease in impedance below a set value for a period of time does not occur. The control module 14 assumes that if by this specified drop or decrease in impedance below a set value for a period of time at step 110 occurs then the reaction event is not stable. The control module 14 then assumes that the tissue has not reacted. The minimum value reached may be any substantially low impedance value or range of values that are complementary to indicate that no tissue reaction occurs such as 10 to 20 Ohms. If the tissue does react by indicating that the impedance is above the minimum set value to indicate that the tissue reacts, the electrosurgical generator 12 passes control to step 108 and the generator enters the energy control mode. If the tissue does not react at step 110, the control will pass to step 102. Optionally, the control module 14 may further have a timer. The timer may provide the control module 14 with a function that once a preset amount of time elapses without any tissue reactance during the time interval, control passes to step 102.

The energy control mode is utilized to reduce vaporization of the liquid or fluid in the tissue. RF energy supplied by the electrosurgical output stage 20 will be controlled in a predetermined fashion to reduce vaporization. The output of the electrosurgical output stage 20 at the energy control mode may match or be complementary to an actual tissue impedance that is monitored by the sensor module 18 or may match to a preset amount or a preset slope of a change of an observed impedance per unit time. The preset amount in the energy control mode at step 108 is impedance that has a preset slope trajectory with time. The preset amount per unit time may be stored in a memory or a recorded medium or may be input or loaded into the system 10 using the user interface 16.

The preset amount has a preset slope trajectory that is accessed from a database or is input using the user interface 16 or is the integral of impedance over time (dz/dt) at step 112. The control module 14 thus adjusts the output of the electrosurgical output 20 and/or the power from the power supply 22 to match the preset slope trajectory at step 112 to modulate the RF energy output from the electrosurgical output 20 at the outset or initial conditions of operation. Control will then pass back to step 104 to determine the tissue impedance at step 104 at a subsequent time.

Figure 7:
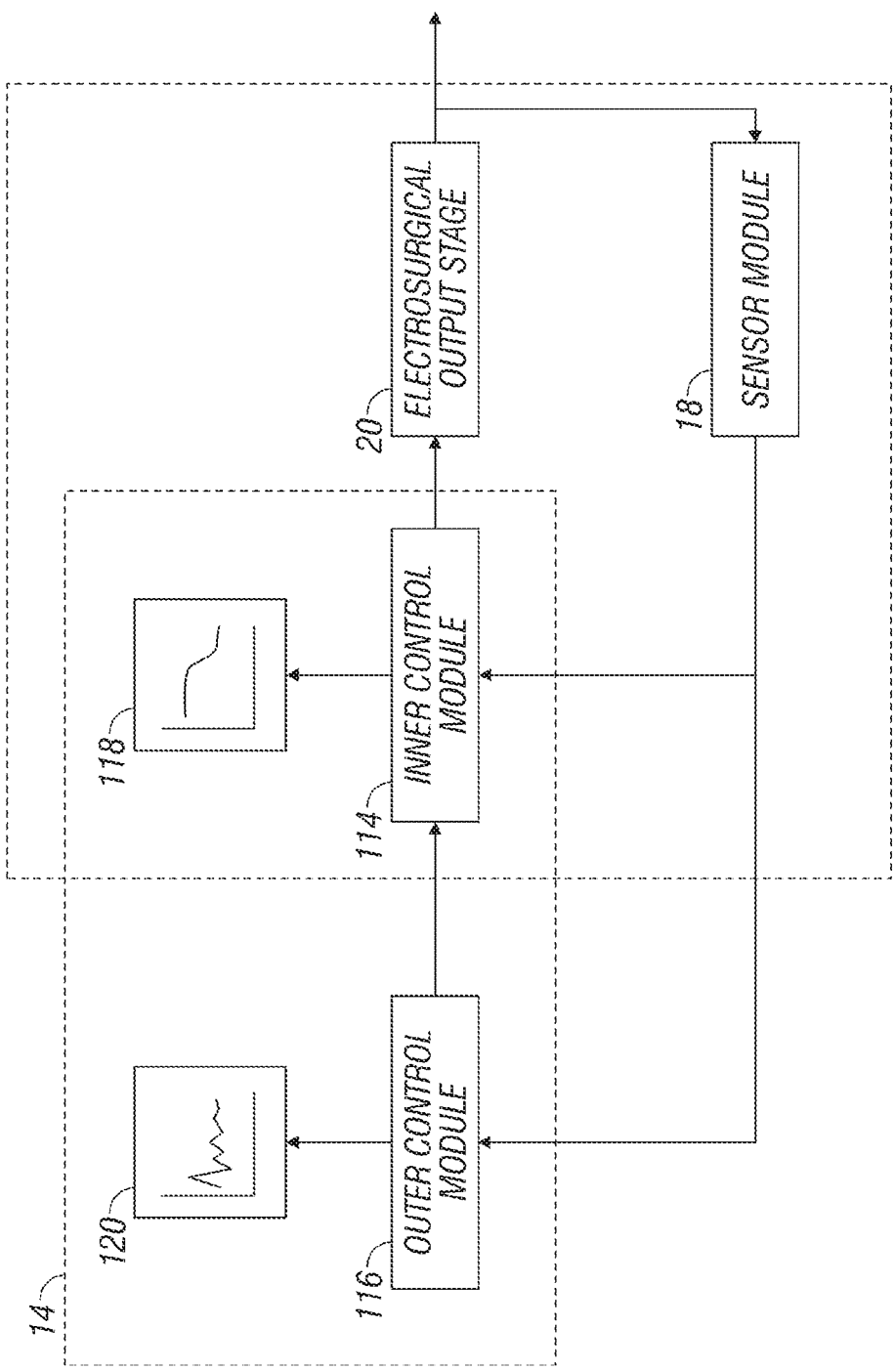
FIG. 7 is a diagram of a control system in accordance with yet another aspect of embodiment of the disclosure.

Referring now to FIG. 7, there is shown a block diagram of another embodiment of the control module 14 having two control loops or an inner loop and an outer loop. The terms "inner" and "outer" form no spatial limitations to the control module 14 and are simply to distinguish between modules of the control module. The inner loop is controlled by an inner loop control module 114 and the outer loop is controlled by a second outer loop control module 116. Both are software modules that are controlled by a processor or other suitable analog circuit of the control module 14. Both the inner control module and the outer control module receive signals from the sensor module 18 as is known in the art. The inner loop control module 114 controls one or more parameters and controls a variable of the generator.

The inner loop control module 114 continually receives real time signals or sensed values from the sensor module 18. The inner loop control module 114 also has a map of continuous values 118. The inner loop control module 114 consults with the map 118. The inner loop control module 114 obtains a desired inner loop value for the impedance or other parameter currently being sensed and derived by the signal being output by the sensor module 18. The inner loop control module 114 uses an algorithm to compare real time sensed values to the desired inner loop values and then outputs a control signal to the electrosurgical output stage 20. The control signal may control one or more parameters of the electrosurgical generator 10 such as for example current, power, voltage, duty cycle, frequency, waveform shape and other parameters.

The outer loop control module 116 is layered over the inner loop control module 114 and provides for an additional control of a variable for reaching a desired output value or effect. The outer loop control module 116 continually receives sensed values, such as current, voltage and temperature from the sensor module 18 at a time (t seconds), (t+1 seconds), (t+2 seconds), (t+3 seconds) for a predetermined amount of time etc. The outer loop control module 116 then performs calculations of the sensed values and stores the values.

The stored values include a value for a change in impedance (dz/dt) that is obtained in accordance with: dz/dt=(z×z(old))/(t×t(old)), wherein Z is impedance measure at time t, and wherein Z(old) is a previous impedance reading being measured at time t(old).

The outer loop desired value for a control value is obtained by accessing a stored map of continuous values shown as reference numeral 120. The map 120 stores a desired rage of parameters including a change in impedance per unit time. The desired rate of a change in impedance per unit time or dz/dt is stored in the map 120, may be constant, or may depend on a stage of the tissue seal cycle or may change over time. One skilled in the art should appreciate that the tissue is in a dynamic state during a surgical procedure and the outer control module 116 monitors a rate of change throughout the procedure, and stores such a change in map 120.

The outer loop control module 116 compares a real time sensed value of a rate of change in the impedance at time (t) to the respective desired value at time (t) obtained from the map 120. The outer loop control module 116 then determines if a desired outer value is met. If not met the control module 116 determines the ratio of a difference between the real time value and the desired outer value to the desired outer value.

If the desired outer value is not met, the outer loop control module 116 then generates a set point value. The set point value is provided to the inner loop control module 114. The set point value may be raised when the real time value for the rate of change of impedance is lower than desired. The set point value may be a ratio signal. The ratio signal is applied to the control signal or for altering the inner map 118 by raising or lowering a plotted curve of the inner map along a Y axis to form an altered inner map value.

The ratio signal is a proportional integral derivative control signal as is known in the art as (PID). The inner loop control module 114 reacts instantaneously and accesses the altered inner map values or series of inner mapped values. The inner loop control module 114 obtains a desired inner value from the outer loop and makes a comparison. The comparison is between the real time value of the control variable and the desired value. The inner control module then generates an RF command for the control variable without exceeding the desired inner value, and outputs the RF command to the electrosurgical output stage 20 for controlling voltage, current and/or power needed for achieving a desired tissue effect. The outer loop control module 116 uses the real time value of rate of change of impedance, temperature, rate of change of temperature, and/or total energy delivered to determine if a desired outer value has been reached which indicates completion of a tissue seal. Upon determination of seal completion, a stop signal is generated for stopping the sealing process. The outer loop continues to monitor, receive and process sensed values from the sensor module 18.

A control of current, voltage and/or power by the inner loop control module 116 improves system stability and control capabilities in low impedance ranges which are critical for seal initiation. Such low impedance ranges are about 0 to 20 ohms. The outer loop control module 116 enhances the control module's ability to control sealing in accordance with desired trends or events, to change seal intensity by changing the rate of change of impedance, and to enhance uniform sealing of tissue, i.e., normalize tissue in terms of variability, including tissue hydration, volume and composition.

With feedback control and continuous sensing of the tissue's condition, there is not a need to switch control variables (i.e., low/high end break points), which improves system stability as explained above.

Referring now again to the energy control mode as shown as step 108 in FIG. 6, the outer loop control module 116 matches the impedance monitored to a preset slope trajectory by accessing a stored preset slope trajectory using values stored in map 120 as indicated by step 112 in FIG. 6. Thereafter, the outer loop control module 116 outputs the matched preset slope trajectory by generating a ratio signal to the inner loop control module 114. The ratio signal controls the RF signal using the matched preset slope trajectory. The outer loop control module 116 then continues to determine the tissue impedance. A significant advantage of the present disclosure is that the control module 14 in this manner may continually adjust to changes in tissue conditions without any "pop" or vaporization of the fluid in the tissue. The control system 10 can apply RF energy that is effectively controlled by one or more characteristics of the tissue rather than one or more program instructions that are independent of the characteristics of the tissue.

When in energy control mode, the control system 10 will continuously monitor for a drop in impedance below a predetermined value over time, signifying the reaction was not stable. The delivered output power will continue to be adjusted in accordance with the slope trajectory. When the tissue impedance, however increases above a predetermined level, the impedance slope trajectory stored in map 120 is recalculated. Once the tissue impedance is sensed to increase above the predetermined level, the "y" axis of the map 120 is recalibrated. The zero-point of the graph in map 120 is aligned with the time point "t" (threshold point), i.e., the point in time where the impedance signal calculated by the inner loop control module 114 increases above the predetermined or threshold point. After a stable reaction point is identified, the associated time that the impedance or signal passed through the threshold is recorded by the outer control module 116 in the map 120. This threshold time marks the initial slope trajectory point as the "t" (threshold point) in the map 120. The outer control module 116 then uses the initial slope trajectory point stored in the map 120 to control the inner control module 114 and applies the ratio signal from that point onwards so that data previously recorded from the initial slope trajectory point can be disregarded.

Thereafter, this correction or reset can lead to a RF pulsing that is effectively controlled by the tissue rather than a preset software to avoid any vaporization of fluids in the tissue at the initial setting. It is envisioned that the present disclosure algorithm, system and method described herein can be used with both the monopolar and bipolar vessel sealing system or tissue fusion devices such as those described in commonly owned U.S. patent application Ser. Nos. 10/460,926, 10/873,860 and U.S. Provisional Ser. No. 60/722,177. The entire contents of all of which are herein incorporated by reference in their entirety.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A method for controlling a surgical energy supplied to tissue using a surgical instrument, the method comprising:
applying a low power pulse of energy to tissue;
determining tissue impedance based on a reaction of the tissue to the low power pulse;
determining an initial set of parameters based on the tissue impedance;
applying a pulse of energy to the tissue according to the initial set of parameters;
measuring a transient pulse width of the pulse of energy; and
determining whether an amplitude of the pulse of energy is less than an ending amplitude.

2. The method of claim 1, further comprising:
comparing the transient pulse width to a threshold; and
adjusting a dwell time of the surgical instrument based on the comparison of the transient pulse width and the threshold.

3. The method of claim 2, wherein adjusting the dwell time of the surgical instrument includes increasing the dwell time of the surgical instrument in response to the transient pulse width being above the threshold.

4. The method of claim 2, wherein adjusting the dwell time of the surgical instrument includes decreasing the dwell time of the surgical instrument in response to the transient pulse width being below a threshold.

5. The method of claim 1, further comprising:
preventing further pulses of energy from being supplied to the tissue in response to the amplitude of the pulse of energy being less than the ending amplitude.

6. The method of claim 1, further comprising:
determining whether the tissue impedance is less than a low impedance threshold.

7. The method of claim 6, further comprising:
preventing further pulses of energy from being supplied to the tissue in response to the tissue impedance being less than a low impedance threshold.

8. The method of claim 1, further comprising:
determining whether the tissue impedance is greater than a high impedance threshold.

9. The method of claim 8, preventing further pulses of energy from being supplied to the tissue in response to the tissue impedance being greater than a high impedance threshold.

10. The method of claim 1, further comprising:
applying one or more further pulses of energy to the tissue.

11. The method of claim 10, further comprising:
measuring an application time, the application time being a time period during which the one or more further pulses of energy are applied to the tissue.

12. The method of claim 11, further comprising:
determining whether the application time exceeds a max energy application time.

13. The method of claim 12, further comprising:
discontinuing application of the one or more further pulses of energy to the tissue in response to the application time exceeding a max energy application time.

14. The method of claim 10, further comprising:
measuring a transient pulse width of the one or more further pulses of energy.

* * * * *